US007249001B2

(12) United States Patent
Heliot et al.

(10) Patent No.: US 7,249,001 B2
(45) Date of Patent: Jul. 24, 2007

(54) PROCESS FOR ESTIMATING THE MOTION PHASE OF AN OBJECT

(75) Inventors: Rodolphe Heliot, Grenoble (FR); Dominique David, Claix (FR); Bernard Espiau, Sainte Agnes (FR); Roger Pissard-Gibollet, Le Touvet (FR)

(73) Assignee: Commissariat a l'Energie Atomique, Paris (FR)

( * ) Notice: Subject to any disclaimer, the term of this patent is extended or adjusted under 35 U.S.C. 154(b) by 0 days.

(21) Appl. No.: 11/416,171

(22) Filed: May 3, 2006

(65) Prior Publication Data

US 2006/0268986 A1  Nov. 30, 2006

(30) Foreign Application Priority Data

May 9, 2005  (FR) .................................. 05 04637

(51) Int. Cl.
G06F 17/10  (2006.01)
G06F 17/00  (2006.01)
G06F 17/40  (2006.01)
G06F 19/00  (2006.01)

(52) U.S. Cl. ...................... 702/189; 324/605; 702/150; 702/179; 702/181

(58) Field of Classification Search ............... 324/602, 324/605, 606; 702/150, 151, 152, 153, 154, 702/179, 181, 189
See application file for complete search history.

(56) References Cited

U.S. PATENT DOCUMENTS

| 3,348,031 | A  | * | 10/1967 | Bates et al. ................. 702/180 |
| 3,400,370 | A  | * | 9/1968  | Fukamachi ................. 702/181 |
| 5,014,220 | A  | * | 5/1991  | McMann et al. ............ 706/45 |
| 5,361,379 | A  | * | 11/1994 | White ......................... 382/227 |
| 6,499,025 | B1 | * | 12/2002 | Horvitz et al. ................ 706/52 |
| 6,560,278 | B2 | * | 5/2003  | Kubo et al. .................. 375/232 |
| 2003/0065409 | A1 | * | 4/2003 | Raeth et al. .................. 700/31 |
| 2003/0186663 | A1 | * | 10/2003 | Chen et al. ............. 455/226.3 |
| 2004/0220769 | A1 | * | 11/2004 | Rui et al. .................... 702/179 |
| 2004/0258154 | A1 |   | 12/2004 | Liu et al. |
| 2006/0268986 | A1 | * | 11/2006 | Heliot et al. ........... 375/240.16 |
| 2007/0016095 | A1 | * | 1/2007  | Low et al. .................. 600/544 |

* cited by examiner

*Primary Examiner*—Edward R Cosimano
(74) *Attorney, Agent, or Firm*—Oliff & Berridge, PLC

(57) ABSTRACT

The process comprises acquisition of experimental data from measurements of physical quantities by means of at least one sensor associated to the object. The process comprises a first reliable estimation of a first range of values with a first method. The process comprises at least one additional estimation of an additional range of values with a different method. The methods each present a predetermined reliability. The ranges of values are successively observed in order of decreasing reliability of the corresponding methods. Each additional range of values is compared with the range of values corresponding to the previous method according to said order. The additional range is chosen as result when the additional range is comprised in the range corresponding to one of the previous methods.

4 Claims, 2 Drawing Sheets

PROCESS FOR ESTIMATING THE MOTION PHASE OF AN OBJECT

BACKGROUND OF THE INVENTION

The invention relates to a process for estimating the motion phase of an object comprising acquisition of experimental data from measurements of physical quantities by means of at least one sensor associated to the object, the process comprising a first reliability estimation of a first range of values with a first method.

STATE OF THE ART

To determine the phase of a periodic motion of a body from physical measurements, one known technique consists in breaking the period down into several zones and in identifying the different zones of the motion by comparison with a reference model. In general, the data from several sensors are used to verify a motion hypothesis built up from different models.

However, known techniques do not enable a satisfactory precision to be obtained in an acceptable time, in particular in the case of determining prosthesis motions. Current techniques do not enable the phase to be calculated in real time, i.e. as the motion takes place, with a short latency time with respect to the motion.

Determining the motion phase enables different postures to be characterized, for example walking, running, sifting or standing. This can serve the purpose for example of preventing a fall or of analyzing a movement in the sporting field to correct the faults.

Apparatuses are thus known comprising gyrometers positioned on a person's lower limbs or trunk. The methods used are for example based on wavelets transformation or on intercorrelation.

OBJECT OF THE INVENTION

The object of the invention is to remedy these shortcomings and in particular to propose a process enabling a motion phase to be estimated with a better precision and in a shorter time than methods according to the prior art.

According to the invention, this object is achieved by the fact that the process comprises at least one additional estimation of an additional range of values with a different method, the methods each presenting a predetermined reliability, the ranges of values being successively observed in order of decreasing reliability of the corresponding methods, each additional range of values being compared with the range of values corresponding to the previous method according to said order, the additional range of values being chosen as result when the additional range of values is comprised in the range corresponding to one of the previous methods.

BRIEF DESCRIPTION OF THE DRAWINGS

Other advantages and features will become more clearly apparent from the following description of particular embodiments of the invention given as non-restrictive examples only and represented in the accompanying drawings, in which.

DESCRIPTION OF PARTICULAR EMBODIMENTS

Figure 1:
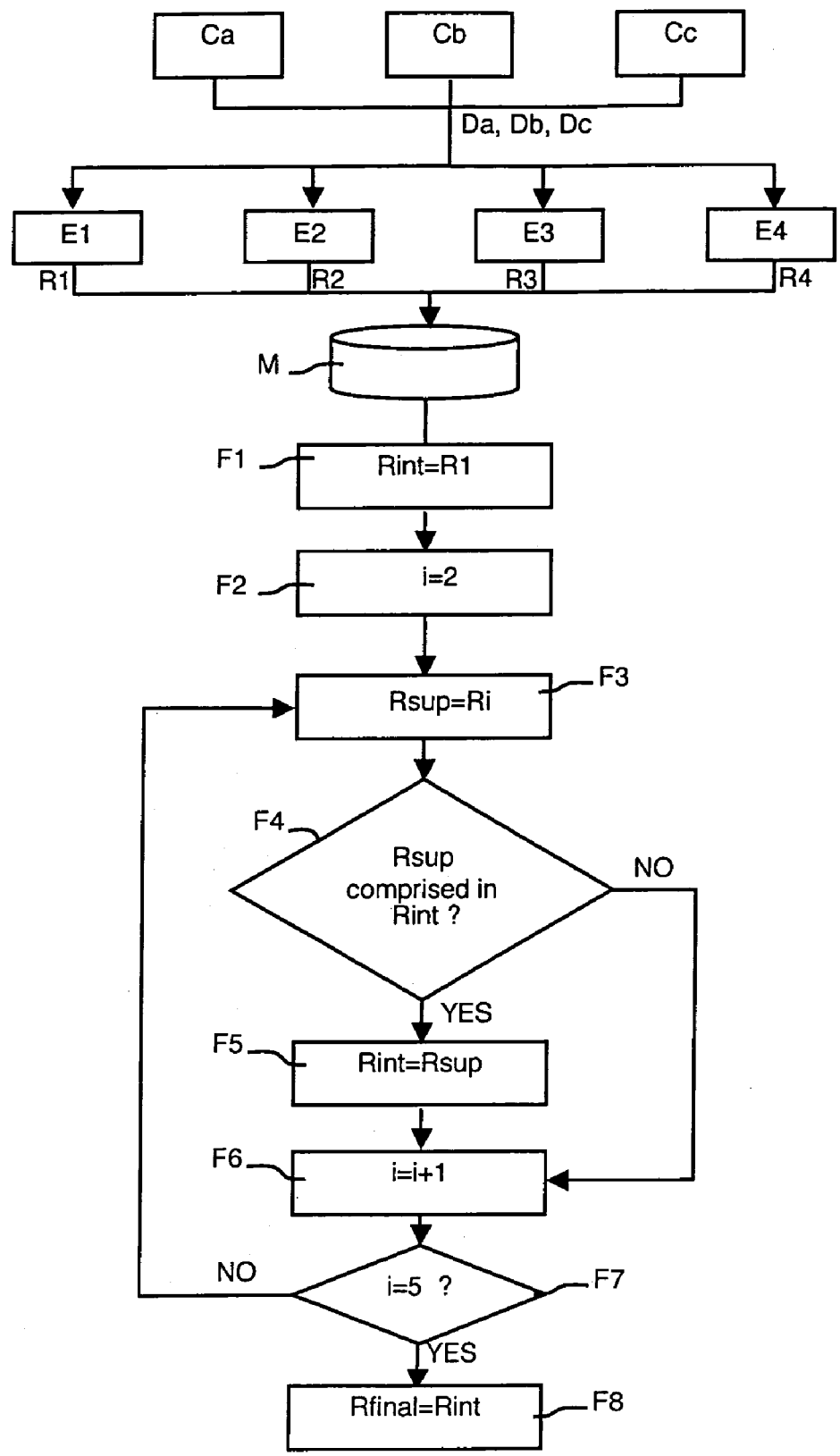
FIG. 1 illustrates a particular embodiment of the process according to the invention.

In FIG. 1, experimental data D (Da, Db, Dc) are acquired from measurements of physical quantities by means of several sensors C (Ca, Cb, Cc), for example accelerometers or magnetometers. The sensors C are associated to the object, for example to an articulated segment, the motion phase of which is to be estimated. What is meant by motion phase is the temporal position in which one is situated at a given moment.

The sensors are for example connected to a portable acquisition system which also enables the analog signals from the sensors to be digitized and which comprises an embedded computer for determining the motion phase.

The experimental data D (Da, Db, Dc) can be previously processed by a Top-hat type transformation.

A first range of values R1 is estimated with a first method by means of a first reliable estimation E1. Second (R2), third (R3) and fourth (R4) additional ranges of values are respectively estimated when second (E2), third (E3) and fourth (E4) additional estimations are made. The estimations can be run simultaneously and the ranges of values R1, R2, R3 and R4 are for example stored in a memory M.

The four estimations are performed with different methods. The estimation methods are characterized by two main properties: their reliability and their precision. A method is considered as being reliable when the result supplied has a high probability of being correct. The result of a method usually corresponds to a range of values. The narrower this range, the more the method is considered to be precise. In general, the more reliable a method, the less precise it is and vice-versa. The reliability can be determined, in known manner, for example empirically. The methods therefore each present a predetermined reliability and are classified in order of decreasing reliability and therefore in order of increasing precision.

The process according to the invention enables the different known methods to be managed and to be combined so as to obtain a reliable and precise result. In particular, the process enables a final result to be developed starting from reliable and fairly imprecise results and then progressing towards a more precise result which is however reliable. This is guaranteed by successive use of increasingly precise (and therefore less reliable) methods, the results of which are only retained when they are compatible with the reliable results of the more reliable methods. The risk of obtaining a very precise but rather unreliable final result is thereby avoided, for the final result must always be comprised in the range of the result at least of the first method, which is reliable. The precision is therefore affined while preserving the initial reliability.

Thus, the first estimation E1 uses the most reliable and therefore the least precise method. The second estimation E2 uses the second method according to the order of reliability. The third estimation E3 uses the third method according to the order of reliability and the fourth estimation E4 uses the least reliable method.

The ranges of values R are then successively observed in the order of decreasing reliability of the corresponding methods. Each additional range (R2, R3, R4) of values is compared with the range of values corresponding to the previous method according to said order.

Thus, in FIG. 1, an intermediate result Rint takes the value of the first range R1 (function F1) and an index i takes the value 2 (function F2). An additional result Rsup takes the value of the range corresponding to the index i (function F3), and therefore of the second range R2 at the first execution of the function F3. Then the intermediate result Rint is compared with the additional result Rsup (function F4).

If the additional result Rsup is comprised in the intermediate result Rint (YES output of F4), the intermediate result Rint takes the value of the additional result Rsup (function F5). The additional result Rsup is therefore accepted.

If the additional result Rsup is not comprised in the intermediate result Rint (NO output of F4), said additional result Rsup is no longer used. The intermediate result Rint can for example be kept, as represented in FIG. 1. In another embodiment described below (FIG. 2) the intermediate result Rint can be replaced by means of a linear progression.

In both cases (YES or NO of F4), the index i is then incremented (function F6). The functions F3 to F6 are repeated so long as the index i is lower than a maximum value (NO output of F7), in particular less than 5 in the case of four estimations being used. In a general manner, the maximum value of the index i for the function F7 is N+1, where N is the number of different methods used.

When the index i is equal to its maximum value (YES output of F7), the final result Rfinal takes the value of the intermediate result Rint (function F8).

Thus, when one of the additional ranges (R2, R3, R3) is comprised in the range corresponding to one of the previous methods (R1, R2, R3), the additional range (R2, R3, R3) is chosen as intermediate result Rint. The final result Rfinal corresponds to the value that the intermediate result Rint takes the last time the function F5 is executed in the succession of steps.

Preferably, estimations by a qualitative analysis method (E1), the wavelets method (E2), the intercorrelation method (E3) and the cyclogram analysis method (E4) are successively used. Each of these methods is well known to a skilled artisan. These methods are based on the principle of comparing a reference model with experimental data acquired from measuring physical quantities. These methods are, in known manner, classified according to an order of decreasing reliability. All these methods provide an estimation of the phase.

Other methods may be used, for example comparison using a sum of the squares of the differences or a method using a matching filter estimating the future value of the phase by varying the progression coefficient of the phase from the measured errors.

Qualitative analysis is generally based on state graphs and on observation of the derivative of the data signal after filtering to eliminate the noise. This method does in fact provide information that is not very precise, but it does enable a first reliable index to be obtained in a very simple and robust manner. The advantage of qualitative analysis is that it enables the motion starting and stopping phases to be detected and enables the speed at which the motion is performed to be estimated very simply. This information can be re-input to a computation using intercorrelation. Generally speaking, results obtained with any one of the methods used can be used in other methods.

The wavelets method enables certain phases of the motion to be detected with precision and reliability, for example placing one's heel on the ground when walking. At this moment, an acceleration peak due to the impact is in fact accompanied by a significant increase of the amplitude of the high-frequency components (compared with the frequencies normally contained in the walking motion) of the observed signal. Thus, in this particular case, the wavelets method provides very precise information on the phase, at a given moment. Moreover, this method enables irregularities and significant discontinuities to be detected.

The intercorrelation method enables the phase to be estimated precisely, but it requires a large computing time which tends to make it rather difficult to use in real time. However this method can be adapted by means of an opening type transformation, which enables slow variations of the signal to be extracted and eliminated and contrasts to be amplified.

The cyclogram analysis method has the advantage of requiring very little computing time and enables the phase to be estimated quickly but this method is subject to noise.

Certain methods can, at certain times, give both a reliable and a very precise result. Such a result can be accepted automatically.

In the case of a cyclic motion, for example walking or swimming, the motion phase is itself periodic. It can then be expressed in terms of percentage in the motion cycle. In this case, observation can involve the current cycle but also the previous cycles. In addition to the additional information supplied, this can enable analysis methods specific to cyclic motions to be used, in particular by cyclogram.

Figure 2:
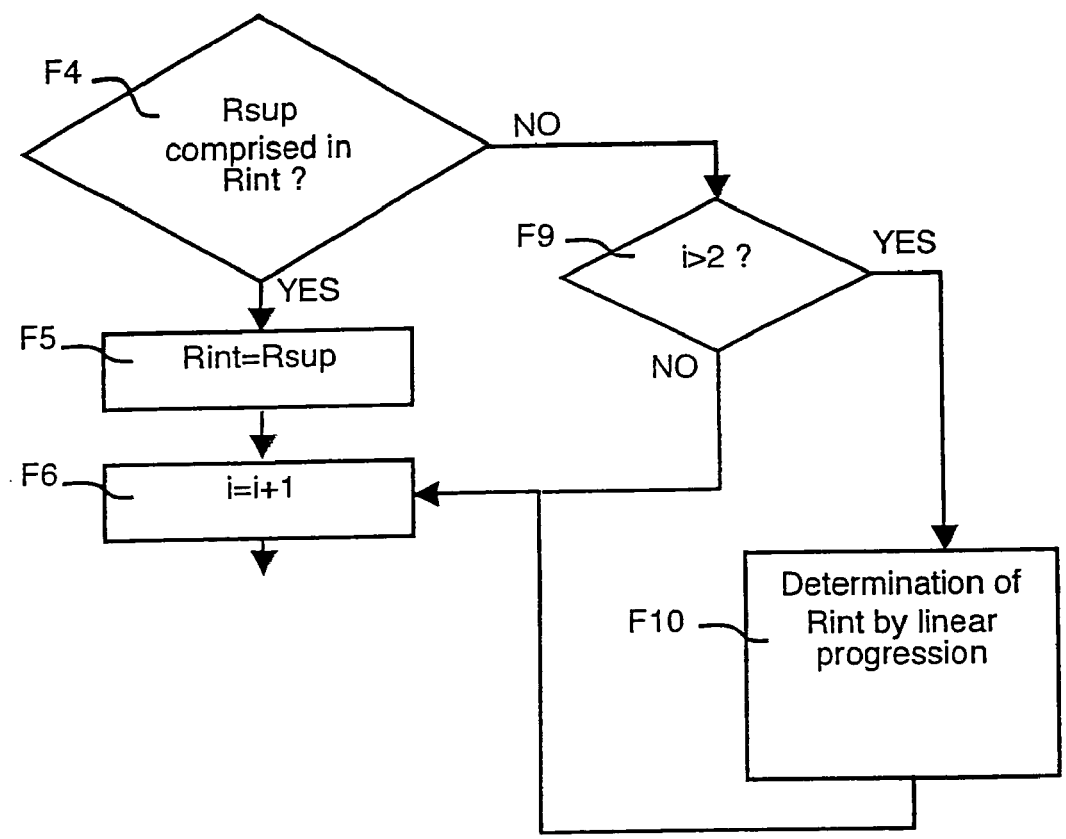
FIG. 2 illustrates additional steps of a particular embodiment of the process according to the invention.

As illustrated in figure 2, when the additional range (R2, R3, R4) that is being observed is not comprised in the range corresponding to the previous method, the additional range of values (R2, R3, R4) can be replaced by a range of values obtained by linear progression from the previous ranges of values. This linear progression can take account of a result obtained for a previous time period. This requires the index i to be greater than 2 (YES output of the function F9), i.e., the first range of values R1 and at least one additional range R2 are available to be able to perform the linear progression. In addition, this additional range R2 must itself be comprised in the first range R1. Thus, as represented in FIG. 2, the intermediate result Rint takes the value of the result of the linear progression (function F10). Then the process continues according to FIG. 1, i.e., the index i is incremented (function F6). If, in function F9, the index i is not greater than 2 (NO output of function F9). the index i is then incremented (function F6).

In a simplified embodiment (not represented), the process is interrupted when the additional range (R2, R3, R4) is not comprised in the range corresponding to the previous method (NO output of F4). In this simplified case, the next additional estimations are not used and the last intermediate result Rint is taken as the final result Rfinal (the NO output of F4 is directly connected to the function F8).

The process can be interrupted for other reasons. For example, when the first estimation E1 enables it to be determined that the object is at a standstill, the process can be stopped. If analysis by wavelets enables the phase to be clearly determined, for example by means of a large wavelet peak, the process can also be stopped.

We claim:
1. Process for estimating the motion phase of an object, comprising:
 acquiring experimental data from measurements of physical quantities by means of at least one sensor associated to the object;
 using the measurement data from the at least one sensor to produce a first reliable estimation of a motion phase with a first range of values by a first method, presenting a first predetermined reliability;

using the measurement data from the at least one sensor to produce at least one additional estimation of a motion phase with an additional range of values with a different method for the at least one additional estimation of a motion phase, the different method presenting a different predetermined reliability;

arranging the ranges of values representing estimations of a motion phase in order of decreasing reliability of the corresponding methods;

comparing each additional range of values with the range of values corresponding to the previous method according to said order;

choosing the additional range of values as a result range of values when the additional range of values lies within the range of values corresponding to one of the previous methods;

applying the result range of values to precisely estimate the motion phase of the object; and reporting the results of the application, wherein the reported precisely estimated motion phase of the object facilitates characterizing the motion of the object.

2. Process for estimating according to claim 1, the first method and the different method successively comprising a qualitative analysis method a wavelets method, an intercorrelation method and a cyclogram analysis method.

3. Process for estimating according to claim 1, wherein, when the additional range does not lie within the range corresponding to the previous method, the additional range is replaced by a range obtained by linear progression from the previous ranges.

4. Process for estimating according to claim 1, wherein, when the additional range does not lie within the range corresponding to the previous method, the process is interrupted.

* * * * *